United States Patent
Kwetkat et al.

(10) Patent No.: US 9,757,701 B2
(45) Date of Patent: *Sep. 12, 2017

(54) METHOD FOR PRODUCING OIL-IN-WATER EMULSIONS FROM SELF-EMULSIFYING GEL CONCENTRATES

(75) Inventors: Klaus Kwetkat, Bergkamen (DE); Britta Jakobs, Langenfeld (DE); Gerd M. Dahms, Duisburg (DE)

(73) Assignee: Sasol Germany GmbH (DE)

(*) Notice: Subject to any disclaimer, the term of this patent is extended or adjusted under 35 U.S.C. 154(b) by 975 days.

This patent is subject to a terminal disclaimer.

(21) Appl. No.: 12/810,042

(22) PCT Filed: Dec. 19, 2008

(86) PCT No.: PCT/DE2008/002115
§ 371 (c)(1),
(2), (4) Date: Oct. 21, 2010

(87) PCT Pub. No.: WO2009/080005
PCT Pub. Date: Jul. 2, 2009

(65) Prior Publication Data
US 2011/0033413 A1 Feb. 10, 2011

(30) Foreign Application Priority Data
Dec. 24, 2007 (DE) .................. 10 2007 063 134

(51) Int. Cl.
| A61K 8/02 | (2006.01) |
| A61K 8/06 | (2006.01) |
| A61K 8/34 | (2006.01) |
| B28B 7/38 | (2006.01) |
| B01F 17/00 | (2006.01) |
| C04B 40/00 | (2006.01) |

(52) U.S. Cl.
CPC ............ B01F 17/00 (2013.01); A61K 8/0208 (2013.01); A61K 8/062 (2013.01); A61K 8/345 (2013.01); B28B 7/384 (2013.01); C04B 40/0039 (2013.01); A61K 2800/21 (2013.01)

(58) Field of Classification Search
CPC ....... B01F 17/00; A61K 8/0208; A61K 8/062; A61K 8/345; A61K 2800/21; B28B 7/384; C04B 40/0039
See application file for complete search history.

(56) References Cited

U.S. PATENT DOCUMENTS

| 4,043,829 A * | 8/1977 | Ratledge ............ C08K 5/20 106/10 |
| 7,611,696 B2 * | 11/2009 | Berg-Schultz ....... A61K 8/4926 424/59 |
| 2005/0136081 A1 | 6/2005 | Kawa et al. |
| 2006/0024248 A1 * | 2/2006 | Spengler ............ A61K 8/31 424/49 |
| 2006/0257334 A1 * | 11/2006 | Dahms ............... A61K 9/5146 424/59 |
| 2007/0248632 A1 * | 10/2007 | Goget ................. A61K 8/0208 424/401 |
| 2008/0166381 A1 | 7/2008 | Weichold et al. |

FOREIGN PATENT DOCUMENTS

| DE | 2928041 A1 * | 1/1981 |
| DE | 10346515 | 4/2005 |
| WO | WO 02/43672 A1 * | 6/2002 |

OTHER PUBLICATIONS

Lewis, Richard J., Sr. (2002) Hawley's Condensed Chemical Dictionary (14th Ed), John Wiley & Sons, pp. 1-3 (enclosed).*
Polysorbate 60, FCC, ScienceLab.com, Inc., Houston, Texas, published online Dec. 17, 2007 @ https://web.archive.org/web/20071217054930/http://www.sciencelab.com/page/S/PVAR/23066/SLP4309, (downloaded Oct. 31, 2013), pp. 1-2 (enclosed).*
The Merck Index, Entry 02031. Cetyl Palmitate.*
J. Adler-Nissen, et al., Apparatus for Emulsion Production in Small Scale and Under Controlled Shear Conditions, Trans IchemE, Dec. 2004, pp. 311-319.
Peter Fischer, et al., Emulsion Drops in External Flow Fields—The Role of Liquid Interfaces, Colloid and Interface Science, 2007, pp. 196-205, vol. 12.
Mikhail V. Ostrovsky, et al., Mechanism of Microemulsion Formation in Syst.with Low Interfacial Tension, J. of Colloid and Interface Sci., Nov. 1984, pp. 206-226, vol. 12.

* cited by examiner

*Primary Examiner* — Snigdha Maewall
(74) *Attorney, Agent, or Firm* — Bushman Werner, P.C.

(57) ABSTRACT

The object of the present invention is a method for producing oil-in-water (O/W) emulsions from self-emulsifying O/W gel concentrates without agitation, such as stirring, or in a laminar flow field.

14 Claims, 2 Drawing Sheets

METHOD FOR PRODUCING OIL-IN-WATER EMULSIONS FROM SELF-EMULSIFYING GEL CONCENTRATES

The present invention relates to a method for producing oil-in-water (O/W) emulsions from self-emulsifying O/W gel concentrates without agitation, such as stirring, for example, or in a laminar flow field.

Emulsions are disperse multi-phase systems formed from at least two liquids which are virtually insoluble in each other. In the simplest case, it is a two-phase system formed from a hydrophilic or polar, for example aqueous, phase and a lipophilic or apolar, oil phase. The inner or disperse phase is present in the form of droplets in the outer, continuous phase. Depending on the type of the inner phase, a distinction is made between oil-in-water emulsions, in which the oil phase is the disperse phase, and water-in-oil (W/O) emulsions, in which the water phase is the disperse phase. In addition to the disperse and the continuous phase, emulsions also contain excipients which facilitate droplet formation and stabilize the droplets formed against coalescence.

The term "microemulsion" is not used in a consistent manner in the current literature. It describes mono-phase systems, bi-continuous emulsions, swollen micelles and other structures which may be clear as well as cloudy. It is not possible to classify an emulsion as a microemulsion simply by the mean droplet size. However, microemulsions are unanimously considered to be thermodynamically stable systems, while other emulsions, in contrast, are kinetically stabilized and from a thermodynamic viewpoint must be described as unstable. Thus, only the thermodynamic definition will be used in the present case.

In the context of the invention, nanoemulsions are emulsions with mean droplet sizes of less than one micrometre. Emulsions with mean droplet sizes of one micrometre or more are termed "macroemulsions" in the context of the present invention.

Emulsions with a sufficiently small droplet size are currently primarily produced in turbulent flow fields which are mainly formed using rotor-stator systems or with the aid of high pressure homogenizers or—and this is still rather unusual—by ultrasound, exploiting the cavitation forces produced thereby.

The term "self-emulsifying" O/W compositions means those compositions which in water spontaneously, i.e. without the input of mechanical energy, such as stirring or even homogenization, break up into an O/W emulsion with discrete droplets which are mobile in the emulsion.

A simple test for establishing whether the composition is self-emulsifying at room temperature, i.e. at 15° C. to 30° C., in particular 20° C. to 25° C., in the context of the present invention, is to bring 5 ml to 10 ml of the composition up to 90 ml to 95 ml with deionized water. If—even without mixing—an O/W emulsion, which may be milky, is formed which does not separate and which is stable for at least one hour, then the composition is self-emulsifying in the context of the present invention.

Systems have already been described for the production of O/W emulsions which are described as self-emulsifying. However, frequently, opinions differ greatly as regards what constitutes "self-emulsifying". In many cases, even with apparent self-emulsifying systems or systems which are described as being self-emulsifying, it is still necessary to stir vigorously or at least to mix the components by shaking.

Liquid pre-concentrates exist, for example, which are typically oils—usually free of water, which contain oil-soluble emulsifiers and are often used in combination with hydrocolloids and electroytes. O/W emulsions which result from such pre-concentrates are often only of average quality as regards stability on storage. The self-emulsifying capability of pre-concentrates is greatly dependent on the solubility of the emulsifier system in the oil phase. Fine oil droplets can frequently only be produced therein when the oil phase and the water-soluble components are specifically selected and their concentrations are matched. Thus, the systems lose flexibility because the concentrates can no longer be used in a sufficiently versatile manner.

Other self-emulsifying systems are based on O/W emulsions which produce self-emulsifying systems when made up with oil. In this case the flexibility is much greater, but necessarily, it is primarily oil that is present in the concentrate, resulting in a distinct limitation for the user of such concentrates. Again, production of the emulsion concentrates requires the use of homogenization tools and thus high shear gradients and high turbulence.

In order to obtain full flexibility both as regards the emulsifiers and as regards the oil phase, the object of the present invention is to provide a self-emulsifying concentrate that allows the emulsifiers or surfactants to be freely selected, whereby the oil components and naturally also the electrolytes and their concentrations can be selected from a wide range. A wide range of choice of hydrocolloids that can be used would also be desirable, both as regards the desired viscosity and also skin feel and any desired hygrostability of the dried emulsions.

At the same time it would be desirable to obtain a concentrate that meant that expensive homogenization devices such as rotor-stator or high pressure homogenizers could be dispensed with, and which meant that processing could be carried out at higher temperatures, but in particular also at room temperature. In accordance with one embodiment, as small as possible a mean droplet size—minimum mean droplet diameter of less than 1 micrometre—should be aimed for, without having to dispense with an intermediate self-emulsifying concentrate stage.

Furthermore, concentrates should be provided wherein, by diluting with water and adding further substances, emulsions of consistent quality can be produced, wherein the production can be carried out continuously as well as batchwise. Both production methods should allow rapid, reliable quality control in order to guarantee a constantly high, predictable emulsion quality.

Surprisingly, the problem outlined above is solved by the present invention which provides a method for preparing self-emulsifying gel concentrates and nanoemulsions or macroemulsions obtained therefrom. The method is characterized by the following steps:

(a) preparing an emulsifier concentrate (A) containing at least:
  (A.1) 0 to 80% by weight, preferably 0.1% to 75% by weight, of one more polyols (P);
  (A.2) 0.01% to 99% by weight, preferably 50% to 70% by weight, of water (W); and
  (A.3) 1% to 80% by weight, preferably between 5% and 40% by weight and in particular between 10% and 30% by weight of one or more ionic surfactants (I) and/or one or more non-ionic surfactants (N), preferably both;
  each with respect to the emulsifier concentrate (A);
(b) bringing an oil phase (O) into contact with the emulsifier concentrate (A) in a laminar flow field to obtain a self-emulsifying O/W gel concentrate (G) with an oil content of more than 5% by weight, preferably 60% to 99% and particularly preferably 80% to 98% by weight;

(c) bringing the O/W gel concentrate (G) into contact with water, which may also contain further additional substances, in order to obtain, spontaneously without the action of shear forces or more expeditiously with the assistance of a stirrer but in a laminar flow field, an O/W macro- (M) or nano- (C) emulsion.

Preferred nanoemulsions are those with mean droplet sizes (determined by static laser light scattering in accordance with DIN/ISO 13320) of under 1.000 nm, preferably less than 500 nm.

The emulsifier concentrate (A) is homogeneous at room temperature but not necessarily isotropic. It must not exhibit any separation phenomena over a time period of 2 hours and contains 0.01% to 99% by weight, preferably 1% to 80% by weight, in particular 5% to 40% by weight and more particularly preferably 10% to 30% by weight or 20% to 30% by weight of water. In particular, the percentage of emulsifier concentrate (A) in the self-emulsifying gel concentrate (G) is 1% to 40% and more particularly preferably 2% to 20% by weight.

The surfactant percentage in the emulsion resulting from spontaneous emulsion of the self-emulsifying gel (G) in water is <10%, preferably <5%, particularly preferably <3% and more particularly preferably <2%. The oil component content of the self-emulsifying gel concentrate (G) is 60% to 99% by weight, preferably 80% to 98% by weight and particularly preferably 84% to 96% by weight.

The self-emulsifying gel concentrates (G) may be extraordinarily stable on storage and can be used like a masterbatch. They are stable on storage across a wide range of temperatures. They may be both clear and cloudy.

The self-emulsifying gel concentrates (G) produced in accordance with the invention are characterized in that they can be produced by bringing oil components together with the emulsifier concentrate (A). The oil component content is preferably above the critical phase volume ratio which would be expected to result in inversion of the emulsion according to the definition by Ostwald (Wa Ostwald, Beiträge zur Kenntnis der Emulsionen [Contributions to Emulsions], Z Kolloid, 6 (1910), 103-109).

The gel concentrates can be produced simply by mixing the emulsifier concentrate (A) with the oil components, maintaining a laminar flow regime. In this respect it is possible to operate both batchwise and continuously; it is only mixing in a laminar flow zone that has to be ensured. The size of the mixing apparatus is of little consequence; conventional mixing technology can be used; the emulsions of the invention are also suitable for continuous production in microprocessing apparatus.

Despite the very high oil concentration, the self-emulsifying gel concentrates (G) exhibit an astonishingly high conductivity: according to H Junginger et al, typical O/W emulsions with a water content of below 20% by weight do not exhibit conductivity in the micro Siemens range (Aufbau and Entwicklung von Salben, Cremes and Emulsionen, Dennatikkurs II [Synthesis and Development of Ointments, Creams and Emulsions, Skin Technology Course II], Arbeitsgemeinschaft für Pharmazeutische Verfahrenstechnik (APV) e. V., H Junginger, Mainz, 1983]. In contrast, the self-emulsifying gel concentrates (G) have a measurable conductivity (at 25° C.) in the micro Siemens range (greater than 1 micro Siemens) with a magnitude of 3 microSiemens, for example.

The production of the self-emulsifying gels is only temperature dependent insofar as the oil components have to be capable of being mixed homogeneously. When producing the gel concentrate (G), the oil phase must be liquid; this determines the production temperature. The oil components employed may dictate a higher temperature.

In general, it is observed that the mean droplet size that can be obtained for the nanoemulsion (C) by self-emulsification of the gel concentrate (G) in water is proportional to temperature. The viscosity of the nanoemulsion (C) can be controlled by the oil content, degree of dilution, and also by hydrocolloids or thickeners. Low viscosity and sprayable (both as a pump spray and as an aerosol spray) emulsions can be produced with an oil phase (O) of up to a maximum of 50% by weight with respect to the nanoemulsion (C), preferably a maximum of 40% by weight with respect to the nanoemulsion (C) and particularly preferably a maximum of 30% by weight with respect to the nanoemulsion (C).

A typical parameter for characterizing the nanoemulsion (C) is the ratio of the oil phase (O) to the surfactant or emulsifier (I+N=E), defined as the parameter Q: O/E=Q. In accordance with the invention, Q is between 1 and 100, preferably between 5 and 50 and particularly preferably between 7 and 35.

Furthermore, the surface area of the particle ($A_p$), determined from the particle size determination based on laser light scattering assuming a spherical particle structure, is defined as follows: $A_p(emul)=k \times exp(k'+E)$, where k' is the material constant, in $m^2$ of particle surface per gram of emulsion. For the nanoemulsions of the invention, as a rule $A_p$ is between 5 and 2000, preferably between 10 and 1000 and particularly preferably between 20 and 800 $m^2/g$.

In the nanoemulsions (C) of the invention, as a rule, the dispersed oil phase is in the form of small fragments (compartments) with a mean of between approximately 10 nm and 10 micrometres, preferably between 200 nm and 5 micrometres, particularly preferably between 300 nm and 1.5 micrometres and more particularly preferably under one micrometre.

They are stable in freeze-thaw cycles (5 times, −18° C. to 40° C. with at least 12 h at each temperature) and stable on storage at room temperature as well as at higher temperatures such as 40° C. and 50° C.

The particular structure of the dispersed oil phase particles of the nanoemulsions of the invention means that drying differs from that for conventional emulsions. Since the conductivity increases during drying, the process is very different from that of conventional emulsions in that an equilibrium value for the conductivity (which is not equal to zero) is obtained at much shorter drying times.

The corresponding measuring apparatus is shown in FIG. 1;

FIG. 3 shows the freeze fracture (freeze fracture TEM) of a conventional O/W emulsion with the following composition:

| A) | |
|---|---|
| Imwitor 380 (Glyceryl Cocoate/Citrate/Lactate) | 3.0% |
| Miglyol 812 (Caprylic/Capric Triglyceride) | 5.0% |
| Cosmacol EMI (Di-Cl2-13 Alkyl Malate) | 2.5% |
| Cosmacol EOI (C-12-13 Alkyl Octanoate) | 3.0% |
| Avocado oil (Persea Gratissima oil) | 3.0% |
| Cyclomethicone | 1.5% |

-continued

| B) | |
|---|---|
| Water (Aqua) demin. | ad 100.0% |
| Xanthan Gum | 0.5% |
| Glycerin | 6.0% |

Figure 1:
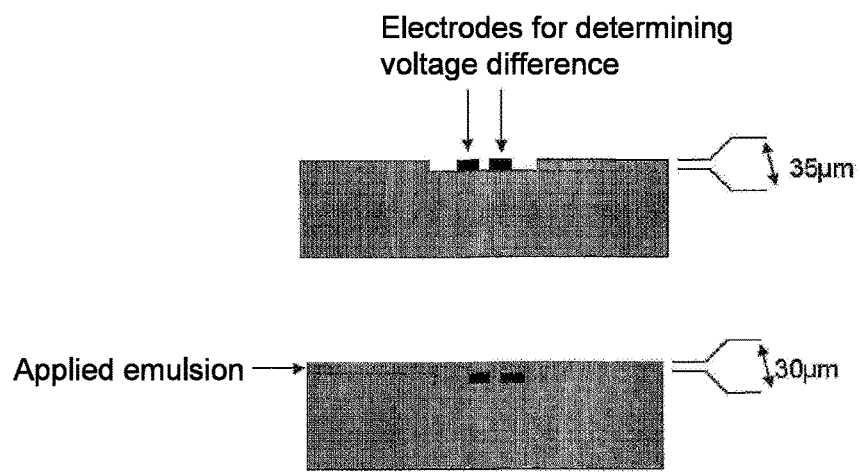
Figure 2A:
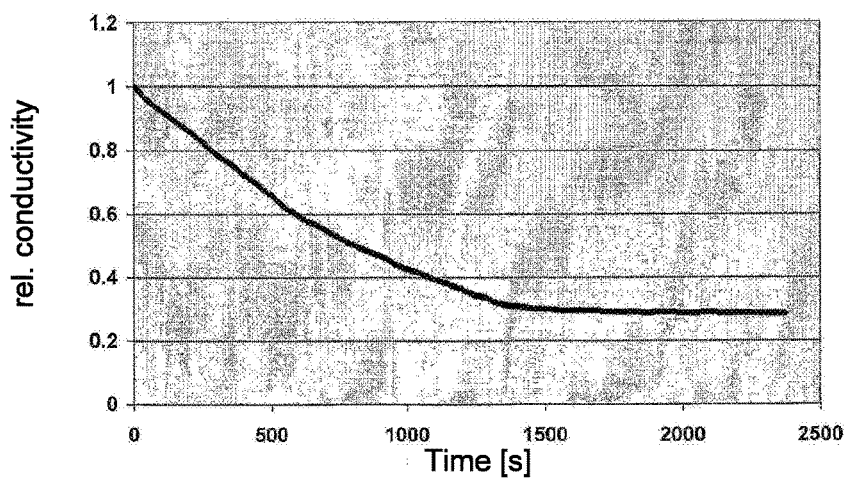
FIG. 2 shows conductivity curves for drying conventional O/W emulsions (FIG. 2a) and the nanoemulsions of the invention (FIG. 2b)
Figure 2B:
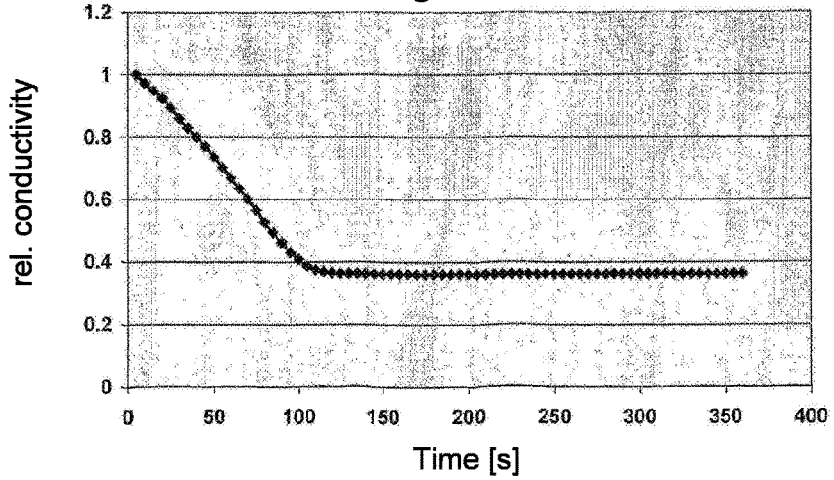
Figure 3:
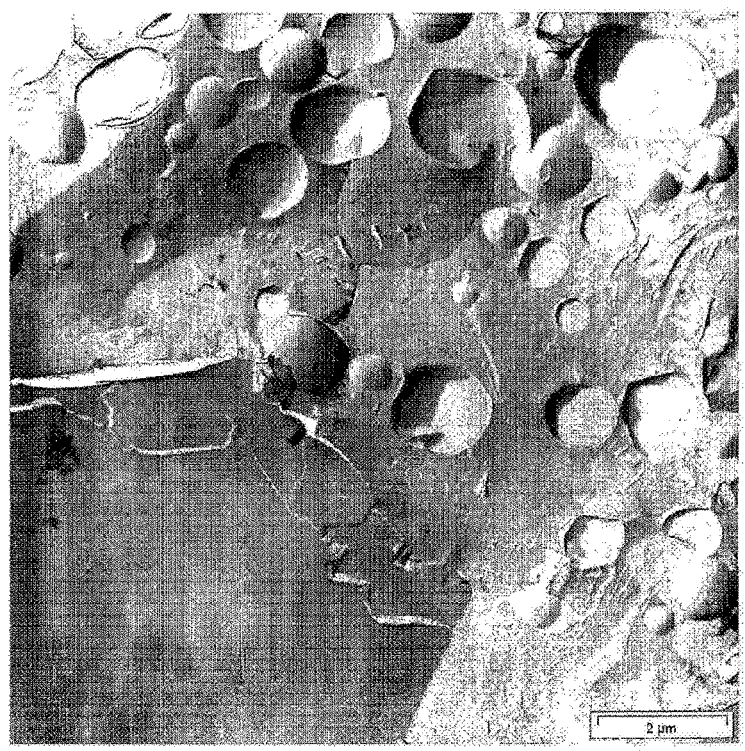
FIGS. 3 and 4 show freeze fractures.
Figure 4:
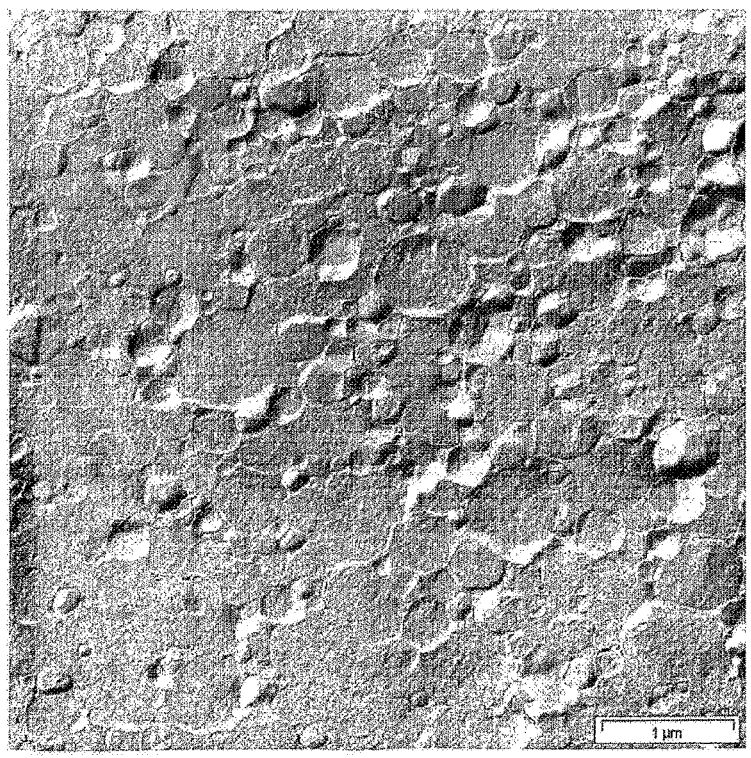

| C) | |
|---|---|
| Tocopheryl Acetate | 1.0% |
| Fragrance | q.s. |
| Preservative | q.s. | and FIG. 4 shows the freeze fracture for Example 4 of the invention.

Phases A) and B) are heated separately to 70° C. and phase B) is mixed for approximately 2 minutes to homogenize it (with an Ultra Turrax rotor-stator mixer). Next, it is cooled and phase C) is added; homogenization as described above is carried out for a further 1 minute. The mean droplet size is 1.5 micrometre.

Because of the particular structure of the dispersed oil particle, when the nanoemulsions (C) are dried, surprising memory effects are usually observed: if a nanoemulsion (C) is dried at 25° C. and under atmospheric pressure, the water evaporates off until the state of the original gel concentrate (G) is obtained. Under the conditions given, this remains stable for at least 24 hours and is self-emulsifying, as indeed it is directly after production thereof. In this case, the original particle size distribution—characteristic of the corresponding gel concentrate—of the dispersed oil phase is re-established. This procedure can be repeated any number of times without changing the particle size distribution. This memory effect significantly distinguishes the nanoemulsions (C) of the invention from conventional emulsions which separate irreversibly when dried in this manner.

The internal structure of the dispersed oil phase particles of the nanoemulsions (C) of the invention is distinguished from that of prior art emulsions in that a coherent film is built up upon drying. This property is advantageous both for sunscreen formulations and for varnishes and dyes, since gloss and scratch resistance are considerably enhanced thereby.

The ionic surfactant I can be anionic, cationic and also amphoteric, and can be used either individually or in combinations. Mutually neutralizing and then precipitating combinations of surfactants are not suitable.

Anionic surfactants in (A) which at room temperature have a tendency to spontaneously form lamellar phases in water in concentrations of <20%, such as Sodium Lauroyl Lactylate (INCI nomenclature), Sodium Cetylsulphate, Sodium Stearoyl Lactylate (INCI nomenclature), are in particular used in combination with other surfactants and are not suitable for use individually.

The polyol content in the emulsifier concentrate (A) is in the range 0' to 80% by weight, preferably in the range 0.1% to 75% by weight, more particularly in the range 10% to 60% by weight and more particularly preferably in the range 20% to 50% by weight, wherein when using only a single surfactant type (I or N), the appropriate concentration is preferably more than 30% by weight.

When polyols are not used, the stability of the nanoemulsions, however, is frequently unsatisfactory in the freeze-thaw cycle. The use of higher electrolyte concentrations also requires the presence of polyols. The polyols preferably contain 2 to 1000 carbon atoms in the (branched if appropriate) hydrocarbon residue and preferably 2 to 50, particularly 2 to 20, particularly preferably 2 to 10 and more particularly preferably 3 to 6 hydroxyl groups. Examples of suitable polyols are alkylene glycols such as ethylene, propylene, butylene, pentylene and hexylene glycols as well as their respective isomers (for example neopentyl glycol), as well as triols such as glycerin and higher polyols such as trimethylol propane, pentaerythritol, polyglycerin, glucoside and polyglucoside, saccharide and their respective alkyl derivatives and mixtures thereof. Polyvinyl alcohols and polyfructoses are also suitable.

Glycerin has proved to be a versatile polyol, but a wide range of other compounds containing multiple hydroxyl groups are also suitable; glycerin-like compounds such as polar glycols are thus particularly suitable. Ethylene glycol, propylene glycol, butylene glycol or pentylene glycol or glycerin derivatives and also PEG derivatives are particularly suitable.

Lactose, dextrose, propylene oxide block copolymers as well as amino-functionalized propylene oxide derivatives are highly suitable, while sorbitol can only be used with a certain limitation of emulsifier efficiency, i.e. when using sorbitol, Q<15.

Emulsifier concentrate A is produced by mixing the components; there is no limitation as regards the mixing tools and temperature ranges.

The oil phase or oil phase-forming oil components in the context of the invention means substances with a surface tension with demineralized water at 25° C. of more than 3 mN·m$^{-1}$, preferably 5 to 69 mN·m$^{-1}$.

Particularly suitable oil components which fall within the above definition are paraffins, esters and mixed esters of silicones or functionalized silicones and organic components, but in particular glycerides and their derivatives. Dimethicones with viscosities>0.0001 mPas and also high viscosity silicon oils with viscosities>60 Pas (both at 25° C.) can be processed to self-emulsifying gels without using specific tools that produce high shear. Distillation residues from petrochemicals, slack waxes and bitumen, can also be mentioned.

The term "self-emulsifying" describes a spontaneous emulsification process which occurs on contact of the self-emulsifying O/W gel with water. This means that when the gel (G) is brought into contact with additional water, the oil phase emulsifies spontaneously, albeit after an initialization period of at most a few minutes, into the form of small fragments with a mean between approximately 100 nm and 10 micrometres, preferably between 200 nm and 5 micrometres, particularly preferably between 300 nm and 1.5 micrometres and more particularly preferably under one micrometre, without additional stirring or other mechanical intervention, within a few minutes to several hours. The spontaneous emulsification results in stable O/W emulsions.

The quantity of oil phase in the nanoemulsion (C) is in the range 0.1% to 70% by weight, preferably in the range 5% to 60% and particularly preferably in the range 10% to 50% by weight.

For surfactant mixtures (I) plus (N), weight ratios of (I) to (N) of between 0.01 to 3 and 3 to 0.01 are particularly suitable. However, only one surfactant (I) or (N) has to be present, but a combination of (I) and (N) in the emulsifier concentrate (A) is preferred. When using different surfactant types, more stable nanoemulsions and also smaller droplet sizes are obtained.

Non-ionic surfactants or surfactant combinations with an HLB (calculated as described by Griffin, J Soc Cosmet Chem 1 (1949) 311-326) of more than 10 are particularly suitable, either alone or, as is more preferable, in combination with an ionic surfactant.

Furthermore, non-ionic surfactants with a particularly high polarity are suitable even when used alone in (A), for example C8 to C14 diamidoethoxylates such as those based on C12/C14 or C8/C10 diamides, containing at least 30 ethylene glycol units.

Examples of suitable examples of surfactants are given below:

Suitable non-ionic surfactants include:

Surfactants which terminate in an alcohol residue, such as:

(1.a) $C_1$- to $C_4$-alkoxylates, including mixtures thereof, of linear or branched, saturated or mono- to tri-unsaturated C10- to C22-alcohols, in particular C12- to C18-fatty alcohol ethoxylates, ethoxylated Lanolin alcohols, polyethylene glycol ether with general formula R—O—(—$CH_2$—$CH_2$—O—)$_n$—R', for example fatty alcohol ethoxylates from the polyethoxylated or polypropoxylated or polyethoxylated and polypropoxylated product group, monoalcohols such as ethoxylated stearyl alcohols, cetyl alcohols, cetylstearyl alcohols and other polyglycols such as ethylene oxide-propylene oxide block copolymers, and polyvinyl alcohols as well as ethoxylated sorbitan esters, cholesterin ethoxylates or allylpolyglycosides with degrees of polymerization of more than 1, and N-allylpyrrolidone derivatives;

(1.b) Fatty alcohol propoxylates with general formula R—O—($CH_2$—$CH(CH_3)$—O—)$_n$—H, polypropylene glycol ether with general formula R—O—(—$CH_2$—CH($CH_3$)—O—)$_n$—R', propoxylated lanolin alcohols, etherified fatty acid propoxylates R—COO—(—$CH_2$—CH($CH_3$)—O—)$_n$—R', esterified fatty acid propoxylates with general formula R—COO—(—$CH_2$—CH($CH_3$)—O—)$_n$—C(O)—R, fatty acid propoxylates with general formula R—COO—(—$CH_2$—CH($CH_3$)—O—)$_n$—H, polypropylene glycol glycerin fatty acid esters, propoxylated sorbitan esters, cholesterin propoxylates, propoxylated triglycerides of alkylether carbonic acids with general formula R—O—(—$CH_2$—CH($CH_3$)O—)$_n$—$CH_2$—COOH, fatty alcohol ethoxylates(X)/propoxylates(Y) with general formula R—O—$X_n$—$Y_m$—H, polypropylene(Y)/ethylene(X)glycol ethers with general formula R—O—$X_n Y_m$—R', etherified fatty acid propoxylates(Y)/ethoxylates(X) with general formula R—COO—$X_n Y_m$—R' and/or fatty acid ethoxylates (X)/propoxylates(Y) with general formula R—COO—$X_n Y_m$—H;

(1.c) Mono-glycerin esters of saturated and/or unsaturated, branched and/or non-branched alkanecarbonic acids with a chain length of 8 to 32, in particular 12 to 18 C atoms, diglycerin esters of saturated and/or unsaturated, branched and/or non-branched allcanecarbonic acids with a chain length of 8 to 32, in particular 12 to 18 C atoms, tri- to deca-glycerin esters of saturated and/or unsaturated, branched and/or non-branched alkanecarbonic acids with a chain length of 8 to 32, in particular 12 to 18 C atoms, monoglycerin ethers of saturated and/or unsaturated, branched and/or non-branched alcohols with a chain length of 8 to 32, in particular 12 to 18 C atoms, di-, tri- to deca-glycerin ethers of saturated and/or unsaturated, branched and/or non-branched alcohols with a chain length of 8 to 32, in particular 12 to 18 C atoms, propylene glycol esters of saturated and/or unsaturated, branched and/or non-branched alkanecarbonic acids with a chain length of 8 to 32, in particular 12 to 18 C atoms, as well as sorbitan esters of saturated and/or unsaturated, branched and/or non-branched allcanecarbonic acids with a chain length of 8 to 32, in particular 12 to 18 C atoms.

Specific examples of this group are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glydol monolaurate, sorbitan monoisostearate, sorbitan monolaurate, sorbitan monocaprylate, sorbitan monoisooleate, saccharose distearate, cetyl alcohol, stearyl alcohol, arachidyl alcohol, behenyl alcohol, isobehenyl alcohol, selachyl alcohol, chimyl alcohol, polyethylene glycol-2-stearylether (Steareth-2), glyceryl monolaurate, glyceryl monocaprinate, glyceryl monocaprylate, alkylphenol polyglycolether (for example Triton X), glycerylmono- and diesters of C12 to C32 Guerbet carbonic acids, preferably C12 to C 24, sugar derivatives (esters and/or ethers of Glucose, saccharose and other sugars), condensation products of aliphatic alcohols containing 8 to 18 carbon atoms, either in linear or branched chain configurations, with ethylene oxide, for example a coconut alcohol-ethylene oxide-condensate with 10 to 30 moles of ethylene oxide per mole of coconut alcohol, wherein the coconut alcohol fraction contains 10 to 14 carbon atoms;

(1.d) Alkylpolysaccharide (APS)-surfactants (for example alkylpolyglycosides); if appropriate, a polyalkylene oxide group binding the hydrophobic and hydrophilic residues may be present; and the C8- to C32-alkyl group, preferably C8 to C18, (i.e. the hydrophobic residue) may be saturated or unsaturated, branched or non-branched and unsubstituted or substituted (for example with hydroxyl or cyclic rings);

(1.e) Polyethylene glycol (PEG)-glyceryl fatty esters, such as those with formula R(O)O$CH_2$CH(OH)$CH_2$ (O$CH_2 CH_2$)$_n$OH, wherein n is on average 5 to 200, preferably approximately 20 to approximately 100, and R is an aliphatic hydrocarbonyl containing approximately 8 to approximately 20 carbon atoms, such as polyethylene glycol (20)glyceryl laurate, polyethylene glycol(21)glyceryl laurate, polyethylene glycol(22)glyceryl laurate, polyethylene glycol(23)glyceryl laurate, polyethylene glycol(6)glyceryl caprate/caprinate, polyethylene glycol(20)glyceryl oleate, polyethylene glycol(20)glyceryl isostearate and/or polyethylene glycol(18)glyceryl oleate/cocoate;

(1.f) Ethoxylated cholesterol derivatives such as polyethylene glycol(30)cholesteryl ether, or even polyethylene glycol(25)soyasterol;

(1.g) Ethoxylated triglycerides such as polyethylene glycol-evening primrose glycerides and polyethylene glycol coconut-, soya-, babassu and almond oil glycerides;

(1.h) Sorbitan esters from the group formed by polyethylene glycol(20)sorbitan monolaurate, polyethylene glycol (20)sorbitan monostearate, polyethylene glycol(20)sorbitan monoisostearate, polyethylene glycol(20)sorbitan monopalmitate and/or polyethylene glycol(20)sorbitan monooleate.

(2) Surfactants terminating in carbonic acids such as, for example:

(2.a) C2- to C4-alkoxylates, including mixtures thereof, of mono- and di-fatty acid glycerides, of fatty acid ethoxylates with general formula R—COO—(—$CH_2$—$CH_2$—O—)$_n$—H, etherified fatty acid ethoxylates with general formula R—COO—(—$CH_2$—$CH_2$—O—)$_n$—R', esterified fatty acid ethoxylates with general formula R—COO—($CH_2$—$CH_2$—O—)$_n$—C(O)—R', partial fatty acid esters and fatty acid esters of polyalcohols and their ethoxylated derivatives, such as polyethylene glycol glycerin fatty acid esters, polyethylene glycol stearyl ether containing 12 to 20 polyethylene glycol units, polyethylene glycol isostearyl ethers containing 12 to 20 polyethylene glycol units, of polyethylene glycol oleates containing 12 to 20 polyethylene glycol units, glyceryl monostearates, sorbitan stearates, glycerylstearyl citrates, sucrose stearates, ethoxylated triglycerides, polyoxyethylene sorbitol fatty acid esters, fatty acid amides, fatty acid alkanolamides, etherified fatty acid propoxylates with general formula R—COO—(—CH$_2$—CH(CH$_3$)—O—)$_n$—R', esterified fatty acid propoxylates with general formula R—COO—(—CH$_2$—CH(CH$_3$)—O—)$_n$—C(O)—R'; and (2.b) Alkylether carbonic acids with general formulae R—O—(—CH$_2$—CH$_2$—O—)$_n$—CH$_2$—COOH and R—O—(—CH$_2$—CH$_2$—(CH$_3$)—O—)$_n$—CH$_2$—COOH, wherein n or the degree of alkoxylation is respectively 5 to 30, in particular 8 to 18. Mixed alkoxylated ether carbonic acids with general formulae R—O—(—CH$_2$—CH$_2$—O—)$_n$—(CH$_2$—CH$_2$—(CH$_3$)—O—)$_m$—CH$_2$—COOH, wherein n and m or the degree of alkoxylation are respectively 5 to 30, in particular 8 to 18. R is linear or branched, saturated to threefold unsaturated, C8 to C32, preferably C8 to C18. For neutralization, alkali and alkaline-earth as well as alkanolamines are preferably used.

(3) Surfactants with other properties, such as, for example:

(3.a) Polyethylene oxide condensates of alkylphenols which, for example, are condensation products of alkylphenols with one alkyl group containing 6 to 20 carbon atoms in either a linear or a branched configuration, with ethylene oxide, wherein the ethylene oxide is present in quantities of approximately 10 to approximately 60 moles of ethylene oxide per mole of alkylphenol;

(3.b) Condensation products (block or randomly distributed structure) of ethylene oxide with the product from the reaction of propylene oxide with ethylene diamines; N,N'-diacylalkylene diamine alkoxylate, ethoxylated fatty amines and alkoxylated N-acylamides as well as N-acyl-N-alkylamide alkoxylates are also suitable;

(3.c) Long-chain tertiary amino oxides with formula [RR'R"N—O], wherein R contains an alkyl-, alkenyl or monohydroxyalkyl residue containing 8 to 18 carbon atoms, from 0 to 10 ethylene oxide units and from 0 to 1 glyceryl units, and R' and R" contain 1 to 3 carbon atoms and 0 to 1 hydroxyl groups, for example methyl, ethyl, propyl, hydroxyethyl and/or hydroxypropyl residues;

(3.d) Long-chain tertiary phosphine oxides with formula [RR'R"P—O], wherein R contains an alkyl, alkenyl or monohydroxyalkyl residue with a chain length in the region of approximately 8 to approximately 18 carbon atoms, 0 to 10 ethylene oxide units and from 0 to 1 glyceryl units, and R and R" are respectively alkyl or monohydroxyalkyl groups containing 1 to 3 carbon atoms; and (3.e) Long-chain dialkyl sulphoxides containing a short-chain alkyl or hydroxyalkyl residue containing 1 to 3 carbon atoms (normally methyl) and a long hydrophobic chain which contains alkyl, alkenyl, hydroxyalkyl or ketoalkyl residues containing 8 to 20 carbon atoms, 0 to 10 ethylene oxide units and 0 to 1 glyceryl units;

(3.f) Non-ionic gemini surfactants, also known as dimeric or twinned surfactants, characterized in that two surfactant units consisting of a hydrophobic group and a hydrophilic group are bonded together via a spacer near the hydrophilic group. For example, N,N'-dialkyl-N,N'-dialkoxylates are particularly suitable.

(3.g) Sorbitan fatty acid esters, polyoxyethylene sorbitan fatty acid esters, lactobionic acid amides, gluconamides, N-methyl gluconamides with a C6 to C32 alkyl residue, preferably C8 to C18, linear or branched, saturated or unsaturated;

(3.h) In combination with highly polar anionic surfactants such as alkylether sulphates or alkyl sulphates or short-chain sulphosuccinates, then even short-chain, preferably branched fatty alcohols with C6- to C15-, particularly preferably C8- to C13-residues, can be used. Alcohols which are sold under the trade names Safol 23, Marlipal 013, Isalchem 123 and Isalchem 125, as well as Marlipal 031, are particularly suitable. Sodium Laureth Sulphate, MIPA- and TIPA-Laureth Sulphate (INCI names) each with 2 ethylene glycol units and also analogues with 3 ethylene glycol units are particularly suitable.

A further peculiarity in combination with highly polar surfactants (as described above) is constituted by alkanol lactates, preferably with mono-branched oxo-alcohols such as the C12- to C13-alkyl lactate (INCI name) Cosmacol ELI. C12-C15 analogues are also suitable.

Anionic Surfactants (1) Fatty acids containing 8 to 30 carbon atoms, glycerin mono- and diesters of saturated and/or unsaturated, branched and/or non-branched alkanecarbonic acids with a chain length of 8 to 32, in particular 12 to 18 C atoms, diglycerin esters of saturated and/or unsaturated, branched and/or non-branched alkanecarbonic acids with a chain length of 8 to 32, in particular 12 to 18 C atoms, monoglycerin ethers of saturated and/or unsaturated, branched and/or non-branched alcohols with a chain length of 8 to 32, in particular 12 to 18 C atoms, diglycerin ethers of saturated and/or unsaturated, branched and/or non-branched alcohols with a chain length of 8 to 32, in particular 12 to 18 C atoms, propylene glycol esters of saturated and/or unsaturated, branched and/or non-branched alkanecarbonic acids with a chain length of 8 to 32, in particular 12 to 18 C atoms as well as sorbitan esters of saturated and/or unsaturated, branched and/or non-branched alkanecarbonic acids with a chain length of 8 to 32, in particular 12 to 18 C atoms, which have been esterified with lactic and citric or tartaric acid and furthermore can be partially neutralized (Imwitor 380, 375, 377, 372 P). Incompletely esterified oligo or polycarbonic acids are also possible, including fruit acids (citric acid, tartaric acid, malic acids) with their mono- or di-esters of linear or branched, saturated or mono- or polyunsaturated C6 to C40 alcohols with their remaining carbonic acid groups then being neutralized. Preferably, sodium, potassium, monoethanol ammonium and monoisopropanol ammonium cations are used for neutralization. Succinic and adipinic acid, maleic acid and fumaric acid are also included;

(2) Alkylether sulphates or their corresponding acids with general formula R—O—(C$_2$H$_4$O)$_x$(—CH$_2$—CH(CH$_3$)—O—)$_n$—SO$_3$—H and alkyl- and alkylether sulphates with respective formulae ROSO$_3$M and RO(C$_2$H$_4$O)$_x$SO$_3$M, wherein R is an alkyl containing approximately 8 to approximately 32, preferably 12 to 18 carbon atoms, and can be linear or mono- or multi-branched, x is 1 to 10, and M is a cation such as ammonium, alkanolamine (for example triethanolamine, mono- and triethanol and mono- and triisopropanolamine), monovalent metal cations (sodium and potassium) and multivalent metal cations such as magnesium and calcium. The alkylether sulphates are typically produced as condensation products of ethylene oxide and mono-alcohols containing 8 to 24 carbon atoms. The alcohols may derive from fats, for example coconut oil or tallow, or they may be synthetic. Lauryl alcohol and linear alcohols derived from coconut oil, as well as oxoalcohols containing C12-C13 mono-branched and C13 alkyl chains based on butene trimerization or propene tetramerization are also preferred herein.

Such alcohols are transformed with between 0 and 10 and in particular 3 molar fractions of ethylene oxide and the resulting mixture of molecular species, for example with an average of 3 moles of ethylene oxide per mole of alcohol, are sulphated and neutralized.

Specific examples of alkylether sulphates are the sodium and ammonium salts of coconut alkyl triethylene glycol ether sulphate, tallow alkyl triethylene glycol ether sulphate and tallow alkyl hexaoxyethylene glycol ether sulphate or of succinates, such as disodium-N-octadecyl sulphosuccinate, disodium lauryl sulphosuccinate, diammonium lauryl sulphosuccinate, tetrasodium-N-(1,2-dicarboxyethyl)-N-octadecyl sulphosuccinate, or the diamylesters of sodium sulphosuccinic acid, dihexylesters of sodium sulphosuccinic acid and the dioctylester of sodium sulphosuccinic acid.

Further preferred alkylether sulphates are those which comprise a mixture of individual compounds, wherein the mixture has a mean alkyl chain length of 10 to 18, preferably 12 to 16 carbon atoms and a mean degree of ethoxylation of 0.1 to 10, preferably 1 to 4 moles of ethylene oxide. Examples are ammonium laureth sulphate, triethylamine laureth sulphate, triethanolamine laureth sulphate, monoethanolaminelaureth sulphate, diethanolamine laureth sulphate, lauric monoglyceride sodium sulphate, sodium laureth sulphate, potassium lauryl sulphate, potassium laureth sulphate, sodium laurylsarcosinate, sodium lauroyl sarcosinate, lauryl sarcosin, cocoyl sarcosin, ammonium cocoyl sulphate, ammonium lauroyl sulphate, sodium cocoyl sulphate, sodium lauroyl sulphate, potassium cocoyl sulphate, triethanolamine lauryl sulphate, triisopropylamine lauryl sulphate, mono-ethanolamine cocoyl sulphate, mono-ethanolamine lauryl sulphate, sodium tridecylbenzene sulphonate and sodium dodecylbenzene sulphonate and sodium laureth sulphate, as well as sodium, potassium and mono-ethanolamine, mono-isopropanolamine salts of C12 to C32 Guerbet acids (produce no liquid crystal phases and can be used alone). Preferably, alkyl sulphates are not employed.

(3) Other suitable anionic surfactants are the water-soluble salts of organic sulphuric acid reaction products (sulphonates) with general formula [R'—SO$_3$— M], wherein R' is selected from the group consisting of linear or branched, saturated aliphatic hydrocarbon residues containing 8 to 24, preferably 10 to 18 carbon atoms and wherein M is a cation. Examples of such surfactants are the salts of an organic sulphuric acid reaction product of a hydrocarbon from the methane series, including iso-, neo- and n-paraffins containing 8 to 24 carbon atoms, preferably 12 to 18 carbon atoms, and a sulphonation agent for example SO$_3$, H$_2$SO$_4$, or oleum obtained in accordance with known sulphonation processes, including bleaching and hydrolysis. Sulphonated alkali metal and ammonium C$_{10-18}$ n-paraffins are preferred.

(4) Further suitable anionic surfactants are the reaction products of fatty acids, esterified with isothionic acid and neutralized with sodium hydroxide, wherein the fatty acids are derived from coconut oil, for example; sodium or potassium salts of fatty acid amides of methyl tauride, wherein the fatty acids are derived from coconut oil, for example.

(5) Mono-, di- and tri-alkylphosphoric acid esters and their alkoxylates (ethoxylates, propoxylates and mixed variations).

(6) Olefin sulphonates containing approximately 10 to approximately 24 carbon atoms formed by sulphonation of alpha-olefins using non-complexed sulphur trioxide, wherein the acid reaction mixture is neutralized so that every sulphone formed is hydrolyzed with the formation of the corresponding hydroxyalkane sulphonate. The alpha-olefins from which the olefin sulphonates are derived are preferably linear mono-olefins containing 12 to 24 carbon atoms, preferably 14 to 16 carbon atoms. In addition to the actual alkene sulphonates and a fraction of hydroxyalkane sulphates, the olefin sulphonates may contain small quantities of other materials such as alkene disulphonates; these are dependent on the reaction conditions, the ratio of the reagents, the nature of the starting olefins and impurities in the olefin starting material and side reactions during the sulphonation procedure.

(7) A further class of anionic surfactants is formed by beta-alkyloxyalkane sulphonates. These surfactants have the following formula:

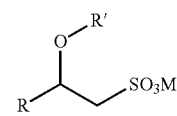

where R is a linear alkyl group containing 6 to 20 carbon atoms, R' is a lower alkyl group containing 1 (preferred) to 3 carbon atoms, and M is a water-soluble cation as described above. Advantageously, the ethoxylated alkylether carbonic acid or its salt which is used can be sodium laureth-11-carboxylate.

(8) A further suitable class of anionic surfactants is formed by anionic gemini surfactants, which are characterized in that two surfactant units consisting of a hydrophobic group and a hydrophilic group are bonded together via a spacer close to the hydrophilic group. Patent documents DE 19943668 and DE 19505368 describe particularly suitable gemini surfactants in detail. Sulphated, carboxymethylated and/or phosphated and then neutralized derivatives of alkylene-N,N'-diacyl-N,N'-dialkoxylates, as well as of diacylene-N,N'-dialkyl-N,N'-dialkoxylates are particularly suitable.

Amphoteric and Zwitterionic Surfactants

Suitable amphoteric surfactants that can be cited are alkylamino alkanecarbonic acids, betaines, sulphobetaines and imidazoline derivatives. "Amphoteric surfactants" also encompasses derivatives of aliphatic secondary and tertiary amines in which the aliphatic residue is linear or branched and wherein one of the aliphatic substituents contains 8 to 18 carbon atoms, and an anionic group that provides water solubility, for example carboxyl, sulphonate, sulphate, phosphate or phosphonate. Alkylamidoamphoacetates and alkylamidoamphodiacetates are also suitable. "Zwitterionic surfactants" includes the derivatives of aliphatic quaternary ammonium, phosphonium and sulphonium compounds in which the aliphatic residues can be linear or branched and wherein one of the aliphatic substituents contains 8 to 18 carbon atoms and one contains an anionic group, for example carboxyl, sulphonate, sulphate, phosphate or phosphonate. A general formula for this compound is:

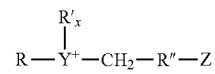

wherein R is an alkyl, alkenyl or hydroxyalkyl residue containing 8 to 18 carbon atoms, 0 to 10 ethylene oxide groups and 0 to 1 glyceryl unit(s); Y is selected from the group consisting of nitrogen, phosphorus and sulphur atoms; R' is an alkyl or monohydroxyalkyl group containing 1 to 3 carbon atoms; X is 1 when Y is a sulphur atom, and X is 2 when Y is a nitrogen or phosphorus atom; R" is an alkylene or hydroxyalkylene containing 1 to 4 carbon atoms, and Z is a residue selected from the group consisting of carboxylate, sulphonate, sulphate, phosphonate and phosphate groups.

Examples of amphoteric and zwitterionic surfactants also include sultaines and amidosultaines. Sultaines and amidosultaines can be used as foam-strengthening surfactants which are mild on the eyes, partially replacing the anionic surfactants. Sultaines and amidosultaines include, for example, cocodimethylpropyl sultaine, stearyldimethylpropyl sultaine, lauryl-bis-(2-hydroxyethyl)propyl sultaine and the amidosultaines, for example cocoamidodimethylpropyl sultaine, stearylamidodimethylpropyl sultaine, laurylamido-bis-(2-hydroxyethyl)propyl sultaine. Amidohydroxysultaines are preferred, such as $C_{12}$-$C_{18}$-hydrocarbylamidopropyl hydroxysultaines, in particular $C_{12}$-$C_{14}$-hydrocarbylamidopropyl hydroxysultaines, for example laurylamidopropyl hydroxysultaines and cocoamidopropyl hydroxysultaines.

Further suitable amphoteric surfactants are aminoalkanoates with formula R—NH(CH$_2$)$_n$COOM, iminodialkanoates with formula R—N[(CH$_2$)$_m$COOM]$_2$ and mixtures thereof; wherein n and m are numbers from 1 to 4, R is $C_8$- to $C_{22}$-alkyl or alkenyl and M is hydrogen, alkali metal, alkaline-earth metal, ammonium or alkanolammonium.

Examples of suitable aminoalkanoates include n-alkylaminopropionates and n-alkyliminodipropionates, examples being N-lauryl-beta-aminopropionic acid or salts thereof and N-lauryl-beta-iminodipropionic acid or salts thereof. Other suitable amphoteric surfactants are characterized by the formula:

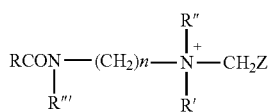

wherein R is $C_8$-$C_{22}$-alkyl or -alkenyl, preferably $C_{12}$-$C_{16}$, R' is hydrogen or CH$_2$CO$_2$M, R" is CH$_2$CH$_2$OH or CH$_2$CH$_2$OCH$_2$CH$_2$COOM, R'" is hydrogen, CH$_2$CH$_2$OH or CH$_2$CH$_2$OCH$_2$CH$_2$COOM, Z is CO$_2$M or CH$_2$CO$_2$M, n is 2 or 3, preferably 2, M is hydrogen or a cation such as alkali metal (for example lithium, sodium, potassium), alkaline-earth metal (beryllium, magnesium, calcium, strontium, barium) or ammonium.

Examples of surfactants with the above formula are monocarboxylates and dicarboxylates. Suitable examples include cocoamphocarboxypropionate, cocoamphocarboxypropionic acid, cocoamphocarboxyglycinate (alternatively denoted as cocoamphodiacetate) and cocoamphoacetate.

Commercially available amphoteric surfactants include those which are marketed under the trade names MIRANOL C2M CONC. N.P., MIRANOL C2M CONC, O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group) and SCHERCOTERIC MS-2 (Scher Chemicals).

Examples of suitable zwitterionic (betaine) surfactants are those which are represented by the following formula (the formula must match the descriptions):

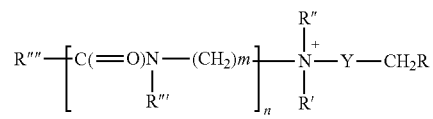

wherein
R is COOM or CH(OH)—CH$_2$SO$_3$M; and
R' is a lower alkyl or hydroxyalkyl;
R" is a lower alkyl or hydroxyalkyl;
R'" is a substituent selected from the group consisting of hydrogen and lower alkyl; and
R"" is a higher alkyl or alkenyl;
Y is a lower alkyl, preferably methyl;
m is an integer from 2 to 7, preferably 2 to 3;
n is the integer 1 or 0; and
M is hydrogen or a cation as described above, for example an alkali metal, alkaline-earth metal or ammonium.

The term "lower alkyl" or "hydroxyalkyl" means linear or branched, saturated aliphatic hydrocarbon residues and substituted hydrocarbon residues containing one to approximately three carbon atoms, such as methyl, ethyl, propyl, isopropyl, hydroxypropyl, hydroxyethyl and the like, for example. The term "higher alkyl or alkenyl" means linear or branched saturated (i.e. "higher alkyl") and unsaturated (i.e. "higher alkenyl") aliphatic hydrocarbon residues containing eight to 20 carbon atoms, such as lauryl, cetyl, stearyl, oleyl, for example. The term "higher alkyl or alkenyl" encompasses mixtures of residues which may contain one or more intermediate linkages such as ether or polyether linkages, or non-functional substituents such as hydroxyl or halogen residues, wherein the residue has a hydrophobic nature.

Examples of benzene surfactants of the above formula wherein n is zero include alkylbetaines, such as cocodimethylcarboxymethyl betaine, lauryldimethylcarboxymethyl betaine, lauryldimethyl-alpha-carboxyethyl betaine, cetyldimethylcarboxymethyl betaine, lauryl-bis-(2-hydroxyethyl)carboxymethyl betaine, stearyl-bis-(2-hydroxypropyl)carboxymethyl betaine, oleyldimethyl-gamma-carboxypropyl betaine, lauryl-bis-(2-hydroxypropyl)-alpha-carboxyethyl betaine. Sulphobetaines can be represented by cocodimethylsulphopropyl betaine, stearyldimethylsulphopropyl betaine and lauryl-bis-(2-hydroxyethyl)sulphopropyl-betaine.

Specific examples are amidobetaines and amidosulphobetaines including amidocarboxy betaines, such as cocoamidodimethylcarboxymethyl betaine, laurylamidodimethylcarboxymethyl betaine, cetylamidodimethylcarboxymethyl betaine, laxnylamido-bis-(2-hydroxyethypcarboxymethyl-betaine and cocoamido-bis-(2-hydroxyethyl)carboxymethylbetaine.

The amidosulphobetaines may be represented by cocoamidodimethylsulphopropyl betaine, stearylamidodimethylsulphopropyl betaine and laurylamido-bis-(2-hydroxyethyl)sulphopropyl betaine.

Examples of suitable cationic surfactants are given below:
Quaternary ammonium compounds, for example, with the following general formula, may be cited:

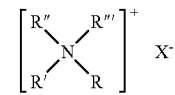

wherein R, R', R" and R'" independently represent an aliphatic group containing 1 to 22 carbon atoms or an aromatic, alkoxy, polyoxyalkylene, alkylamido, hydroxyalkyl, aryl or alkylaryl group containing up to 32 carbon atoms and X is a salt-forming anion such as halogen (for example chloride, bromide), acetate, citrate, lactate, glycolate, phosphate, nitrate, sulphate, methosulphate and alkylsulphate residue. In addition to carbon and hydrogen atoms, the aliphatic groups may contain ether and other groups such as amino groups. The long-chain aliphatic groups containing 12 or more carbon atoms, for example, may be saturated or unsaturated.

Preferably, R, R', R" and R'" are independently $C_1$- to $C_{22}$-alkyl. Particularly preferred compounds are those with two long alkyl chains and two short alkyl chains, or one long alkyl chain and three short alkyl chains.

The long alkyl chains contain 12 to 22 carbon atoms, preferably 16 to 22 carbon atoms, and the short alkyl chains have 1 to 4 carbon atoms, preferably 1 to 3 carbon atoms. Furthermore, alkylpyridinium salts, salts of amino oxides, sulphonium salts and tropylinium salts are suitable. Cetyl-, cetearyl- and behenyl-trimethylammonium chloride, bromide and methosulphate (INCI) are particularly suitable.

Particularly suitable non-ionic or anionic surfactants which can be used which may be cited are Gemini surfactants, wherein in various alkoxylate groups, the respective alkyloxylate groups are randomly distributed or may be arranged in a block structure. With block structure arrangements, it is particularly advantageous for the propoxylate block to be linked up initially.

Structures A.I, A.II and B.III are particularly suitable.

Structures based on amide- or amine-containing spacers.
A.I Gemini Surfactants with General Formula (A.I), Analogous to WO 96/14926:

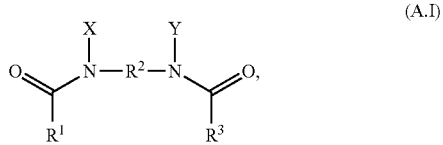

wherein the substituents have the following meaning:
$R^1$, $R^3$ $C_5$- to $C_{25}$-alkyl, branched or non-branched, also unsaturated;
$R^2$ $C_1$- to $C_{12}$-alkylene;
X, Y $(C_2H_4O—)_x(C_3H_6O—)_y$—FR; x+y≥1, x: 0-15, y: 0-10; and
FR —$SO_3M$, —$CH_2$—$CO_2M$, —$P(O)(OM)_2$, H, —$C_3H_6SO_3M$; or
—$CH_2(CHOH)_4$—$CH_2OH$, insofar as x+y=0; wherein M=alkali, (alkyl)ammonium, alkanolammonium, H or ½ alkaline-earth.

A.II Gemini Surfactants with Dicarbonic Acid-Derived Spacers with General Formula (A.II), Analogous to WO 96/25388:

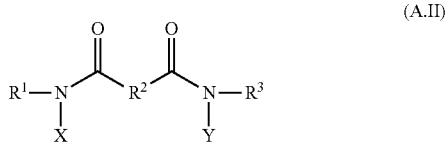

wherein the substituents have the meanings given for general formula (A.I).

A.III Amphoteric Gemini Surfactants with General Formula Analogous to WO 97/31890:

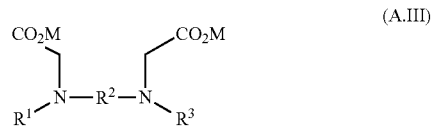

wherein the substituents have the meanings given for general formula (A.I). Gemini surfactants with general formula (A.III) are amphoteric compounds; thus, if they are in an acid environment, they can also become cationic.

Structures based on amide- or amine-containing spacers.
B.I Gemini Surfactants with General Formula (B. I), Analogous to DE 19622612 or JP-A-10-175934:

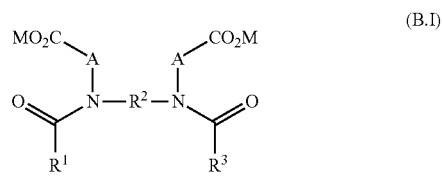

wherein the substituents have the following meaning:
$R^1$, $R^3$ $C_5$ to $C_{25}$-alkyl, branched or non-branched, also unsaturated;
$R^2$ $C_1$- to $C_{12}$-alkyls;
A $CHR^4$, $CH_2$, $C_2H_4$, $C_3H_6$, $C_4H_8$;
$R_4$ residue of an aminocarbonic acid; and
M alkali, (alkyl)ammonium, alkanolanunonium, H or ½ alkaline-earth.

B.II Gemini Surfactants with General Formula (B. II), Analogous to EP 0 708 079:

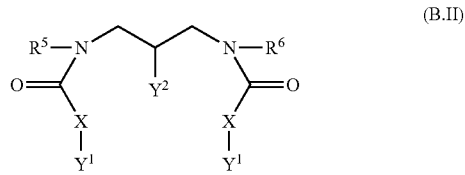

wherein the substituents have the meanings given for general formula (III) and
$R^5$, $R^6$ $C_6$- to $C_{36}$-alkyl, branched or non-branched, also unsaturated;
X alkylene or alkylene group containing 1 to 6 carbon atoms, which may be substituted with a hydroxyl group or a sulphonic acid group or a carboxyl group;
$Y^1$ a sulphonate or sulphate group or a carboxyl group; and
$Y^2$ a hydroxyl group, a sulphuric acid residue or O—(CO)X—COOH.

B.III Gemini Surfactants with General Formula (B. III), Analogous to JP-A-8-311003:

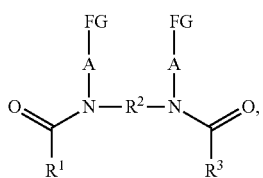

(B.III)

wherein the substituents have the meanings given for general formula (B.I), and
FG is —COOM or —SO$_3$M.

B. IV Gemini Surfactants with General Formula (B. IV), Analogous to JP-A 11-60437:

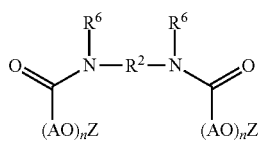

(B.IV)

wherein the substituents have the meanings given for general formulae (B.I) and (B.II), and
AO means alkylene oxide units, i.e. ethylene glycol-, propylene glycol- and butylene glycol-ether units, alone or randomly or blockwise distributed, with n=1 to 20; and
Z means —SO$_3$M, —C$_2$H$_4$SO$_3$M, —C$_3$H$_6$SO$_3$M, —P(O)(OM)$_2$ or —CH$_2$—COOM, —C$_2$H$_4$—COOM.

Structures based on amide or amine-containing spacers.

C.I Gemini Surfactants with General Formula (C.I), Analogous to EP 0 697 244:

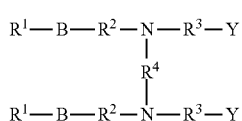

(C.I)

wherein the substituents have the following meaning:
R$^1$ C$_5$- to C$_{25}$-alkyl, branched or non-branched, also unsaturated, hydroxy-substituted or perfluorinated;
R$^2$ C$_1$- to C$_{12}$-alkyls or hydroxy-substituted derivatives thereof;
B an amide group [—C(O)N(R$^2$)— or —N(R$^5$)C(O)—], a carboxyl group [—C(O)O— or —OC(O)—], a polyether group [—(O(R$^6$—O)$_x$—];
R$^5$ represents C$_1$- to C$_4$-alkyl or hydroxy-substituted alkyl or H;
R$^6$ represents C$_2$- to C$_4$-alkyls;
x is a number from 1 to 20;
R$^3$ represents C$_1$- to C$_{12}$-alkyl or hydroxy-substituted derivatives thereof, R$^7$-D-R$^7$ or a polyether group [—(O(R$^6$—O)X—];
R$^7$ represents C$_1$- to C$_6$-alkyls or hydroxy-substituted derivatives thereof;
D represents —O—, —S—, —N(R$^8$)—;
R$^4$ represents alkyls or alkylaryl containing 1 to 12 C atoms or the hydroxy-substituted derivatives or R$^9$-D$^1$-R$^9$;
R$^8$ represents C$_1$- to C$_{12}$-alkyls or hydroxy-substituted derivatives or H or R$^9$-D$^1$R$^9$;
R$^9$ represents C$_1$- to C$_6$-alkyls or hydroxyl-substituted alkyl or H or aryl;

D$^1$ represents —O—, —S—, —SO$_2$—, —C(O)—, [—(O(R$^7$—O)$_x$—], (R$^{10}$)$_t$[N(R$^{10}$)]$_z$ or aryl;
t,z independently represent a number from 1 to 4; and
Y independently represents —SO$_3$H, O—SO$_3$H, —OP(O)(OH)$_2$, —P(O)(OH)$_2$, —COOH, —CO$_2$—C$_6$H$_4$—SO$_3$H and salts thereof.

C.II Gemini Surfactants with General Formula (CII), Analogous to EP 0 697 245:

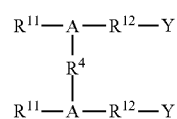

(C.II)

wherein the substituents have the meanings given for general formula (C.I) and
R$^{11}$ represents C$_5$- to C$_{23}$-alkyl, branched or non-branched, also unsaturated, hydroxy-substituted or perfluorinated, or R$^{14}$—B—R$^2$;
R$^{14}$ represents C$_1$- to C$_{12}$-alkyl, branched or non-branched, also unsaturated or hydroxy-substituted derivatives;
R$^{12}$ represents C$_1$- to C$_{12}$-alkyls, branched or non-branched, saturated, optionally non-adjacent unsaturated up to two times, or hydroxy-substituted derivatives, or an amide group [—C(O)N(R$^2$)— or —N(R$^5$)C(O)—], a carboxyl group [—C(O)O— or —OC(O)—], a polyether group [—(O(R$^6$O)$_x$—] or R$^9$-D$^1$-R$^9$; and
A represents —CR$^6$= or —N= with the proviso that when A is —N=, R$^{11}$ represents R$^{14}$—B—R$^2$.

C.III Gemini Surfactants with General Formula (C.III), Analogous to DE 4227391 and DE 19608117

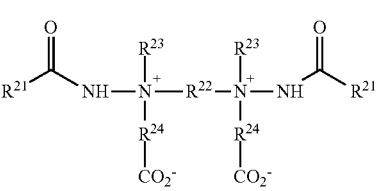

(C.III)

wherein the substituents have the meanings given for general formulae (C.I) and (C.II); and
R$^{21}$ represents C$_5$- to C$_{23}$-alkyl, branched or non-branched, also unsaturated;
R$^{22}$, R$^{24}$ represent C$_1$- to C$_6$-alkylene;
R$^{23}$ represents methyl, ethyl, propyl or a polyether group [—(O(R$^6$—O)$_x$—].

D.I Gemini Surfactants with General Formula (D.I), Analogous to U.S. Pat. No. 5,863,886:

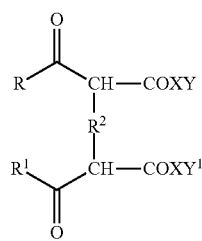

(D.I)

wherein the substituents have the following meaning:

R, $R^1$ represent $C_5$- to $C_{30}$-alkyl, branched or non-branched, also unsaturated, hydroxy-substituted or perfluorinated;

$R^8$ represents $NYY^1$, $-O(R^4O)_xH$ or $-O(R^4O)_x-C(O)-CHR-CHR^1-C(O)NYY^1$.

D.IV Gemini Surfactants with General Formula (D.IV), Analogous to WO 96/25384:

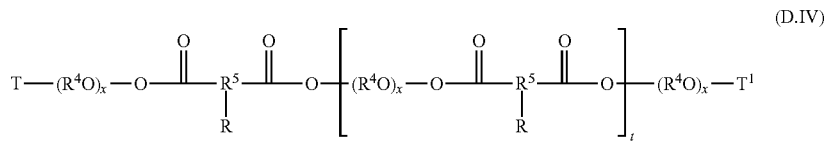

(D.IV)

$R^2$ represents $C_1$- to $C_{10}$-alkylene, aryl and hydroxy-substituted derivatives, a polyether $[-O(R^4O)_x-]$, $-S-$, $-SO_2-$, $-O-$, $-S-S-$, $-O-R^5-O-$ or $-S-R^5-S-$; variable for a direct bond between the two α-carbons;

$R^4$ $C_2$- to $C_4$-alkylene;

$R^5$ $C_1$- to $C_{10}$-alkylene, arylene or alkylarylene, $-N(R^6)-$ or $-(NR^6)-R^7-(NR^6)-$;

$R^6$ represents $C_1$- to $C_6$-alkyl;

$R^7$ represents $C_1$- to $C_6$ alkyl, wherein $R^7$ and $R^6$ may also be part of a heterocyclic ring;

X represents polyether $[-O(R^4O)_x-]$, where x is a number from 1 to 30, $-O-$, NZ;

Z represents $C_1$- to $C_{10}$-alkyl, aryl, allylaryl or H; and

Y, $Y^1$ independently of each other represent H $-CH_2-COOH$ and salts, a hydrocarbon residue containing at least 2 hydroxyl groups such as erythrose, threose, ribose, arabinose, xylose, fructose, lyxose, allose, altrose, glucose, mannose, galactose and their mixtures.

D.II Gemini Surfactants with General Formula (D.II):

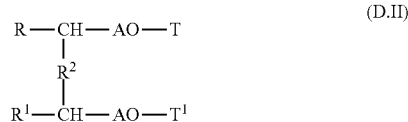

(D.II)

wherein the substituents have the meanings given for general formula (D.I) and:

AO represents $-C(O)-$, $-C(O)-[-O(R^4O)_x-]$, $-CH_2-[-O(R^4O)_x-]$, $-CH_2-O-$;

T, $T^1$ independently represent $-OM$, $-H$, $-CH_3$, $-C_2H_5$, $-SO_3M$, $-CH_2COOM$, $-C_2H_4-COOM$, $-C_3H_6-SO_3M$, $-O-P(O)(OM)_2$; and M represents alkali, ½ alkaline-earth, ammonium, mono-, di-, tri-alkanolammonium or H.

D.III Gemini Surfactants with General Formula (D.III), Analogous to WO 96/16930:

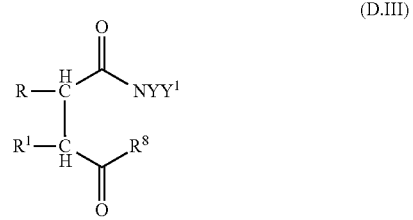

(D.III)

wherein the substituents have the meanings given for general formulae (D.I) and (D.II); and wherein the substituents have the meanings given for general formulae (D.I), (D.II) and (DIU); and t is an integer from 1 to 100, preferably 1 to 20, particularly preferably 1 to 4.

Oil Phase

The oil phase of O/W emulsions with the formulations of the invention are advantageously selected from the group formed by polar oils, for example from the fatty acid triglyceride group, namely glycerin triesters of saturated and/or unsaturated, branched and/or non-branched alkanecarbonic acids with a chain length of 8 to 32, in particular 12 to 18 C atoms.

As an example, the fatty acid triglycerides may advantageously be selected from the group formed by synthetic, semi-synthetic and natural oils such as cocoglyceride, olive oil, sunflower oil, soya oil, peanut oil, rapeseed oil, almond oil, palm oil, coconut oil, castor oil, wheatgerm oil, grapeseed oil, distel oil, evening primrose oil, macadamia nut oil, babassu oil, carrot oil, palm kernel oil and more of the like.

Furthermore, synthetically produced esters can be used of C6- to C32-carbonic acids or hydroxycarbonic acids, linear or branched, saturated or mono- to threefold unsaturated, with di-, or poly-hydroxy compounds, which can be completely saturated with carbonic acids or only partially saturated, but must be at least mono-reacted and must not exhibit any significant surface activity. Particularly suitable compounds in this instance are MCT oils (MCT=mid-chain triglyceride) such as Caprylic/Capric Triglyceride or Butylene Glycol Dicaprylate/Dicaprate and the corresponding propylene glycol variations and also corresponding esters of propylene and butylene glycol. Other suitable compounds are (INCI) Bis-Diglyceryl-Polyacyl-Adipate-1 and -2 as well as their natural precursors lanolin and lanolin oil, as well as lanolin alcohol.

In the context of the present invention, further advantageous polar oil components may further be selected from the group of esters from saturated and/or unsaturated, branched and/or non-branched alkane carbonic acids with a chain length of 3 to 40 C atoms and saturated and/or unsaturated, branched and/or non-branched alcohols with a chain length of 3 to 40 C atoms as well as from the group formed by esters of aromatic carbonic acids and saturated and/or unsaturated, branched and/or non-branched alcohols with a chain length of 3 to 40 C atoms.

Ester oils can advantageously be selected from the group formed by octyl palmitate, octyl cocoate, octyl isostearate, octyldodecyl myristate, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, as well as synthetic, semi-synthetic and natural mixtures of such esters, such as jojoba oil, almond oil, orange oil, macadamia oil, babassu oil, evening primrose oil and other oils, for example. C10 to C36 Guerbet alcohols may also be used as polar oil components.

Furthermore, the oil phase can advantageously be selected from the dialkylether and dialkylcarbonate group; advantageously, for example, dicaprylyl ether (Cetiol OE, Cosmacol OE) and/or dicaprylylcarbonate, for example that with trade mark Cetiol CC obtainable from Cognis, is used.

The oil components may also be a neopentyl glycol diheptanoate, a propylene glycol dicaprylate/dicaprate, a caprylic/capric/diglycerylsuccinate, a butylene glycol-dicaprylate/dicaprate, a C12/C13-alkyllactate, a di-C12/13-alkyltartrate, a triisostearin, a dipentaerythrityl-hexacaprylate/hexacaprate, propylene glycol mono-isostearate, and/or tricaprylin.

Examples of further advantageous oil components are butyloctyl salicylate (for example that marketed under the trade name Hallbrite BHB by C P Hall), hexadecyl benzoate and butyloctyl benzoate and mixtures thereof (Hallstar AB) and/or diethylhexyl naphthalate.

Any admixtures of such oil components are of advantage in the context of the present invention.

Further, the oil phases can advantageously also contain non-polar oils, for example branched and non-branched hydrocarbons and waxes, in particular mineral oil, Vaseline (petrolatum), paraffin oil, squalene and squalene, polyolefins, hydrogenated polyisobutene and isohexadecane. Polydecenes are the preferred polyolefins.

Advantageously, the oil phases can also contain a quantity of cyclic or linear silicone oils or may consist entirely of such oils; in this case, in addition to silicone oil or silicone oils, an additional quantity of other oil phase components is preferable. Silicone oils are synthetic polymeric compounds in which the silicon atoms are bonded together via oxygen atoms. Methyl-substituted polyorganosiloxanes are also known as polydimethylsiloxanes or dimethicone (INCI). Dimethicone is available in various chain lengths or with various molecular weights. Dimethicone oils (INCI) may also be used.

Examples of particularly advantageous polyorganosiloxanes for use in the present invention are dimethylpolysiloxanes [poly(dimethylsiloxane)]. More advantageous compounds are phenylmethylpolysiloxanes (INCI: Phenyl Dimethicone, Phenyl Trimethicone), cyclic silicones (decamethylcyclopentasiloxane, dodecamethylcyclohexasiloxane), which are also denoted Cyclomethicone under the INCI classification, amino-modified silicones (INCI: Amidodimethicone) and silicone waxes, for example polysiloxane-polyalkylene copolymers (INCI: Stearyl Dimethicone and Cetyl Dimethicone) and dialkoxydimethylpolysiloxanes (Stearoxy Dimethicone and Behenoxy Stearyl Dimethicone).

Bitumen mixtures of various viscosities and provenances (from petrochemicals or from natural sources (known as asphaltenes)) may also advantageously be employed. When the softening points are too high, pressurized systems must be used at over 100° C.; however, this does not constitute a limitation upon the use according to the invention. In this case, heat-resistant surfactants must in particular be employed.

It may also be advantageous to use waxes, for example cetyl palmitate, as the sole lipid component of the oil phase. Advantageously, the oil phase is selected from the group 2-ethylhexyl isostearate, octyldodecanol, isotridecyl isononanoate, isoeicosan, 2-ethylhexyl cocoate, C12-15-alkylbenzoate, capryl-caprinic acid triglyceride, dicaprylylether, didoceylether, didecylether.

Further, perfluoroethers, perfluoro-alcohols and -acids and their derivatives, as well as silicone and silane derivatives containing perfluoro groups, may be used alone or as components of the oil phase.

Further, advantageously, esters of hydroxycarbonic acids may be used in the oil phase or as the sole components of the oil phase; particularly preferably, the following are used: alkylcarbonic- and benzoic- as well as salicylic acid esters with C2 to C40, linear or branched, saturated or unsaturated alcohols and mixtures of the various alcohols. The alkyl esters of glycolic acid, lactic acid, citric acid, tartaric acid, benzoic acid, 2-ethylhexanoic acid, malic acids, salicylic acid and benzoic acid are particularly suitable.

Furthermore, the oil phase may also consist of monomers and their polymers and copolymers, vinyl alcohol and its esters, preferably vinyl acetate, vinyl chloride, acrylic acid and its esters, methacrylic acid and its esters, ethylene, alpha and mid-chain C2 to C22 olefins; ethylene, propylene, butylene, styrene, cyclopentadiene and/or butadiene are particularly suitable.

The viscosity of the nanoemulsion (C) obtained by diluting the self-emulsifying gel (G) can be controlled with the aid of any available hydrocolloid and thickener.

These hydrocolloids and thickeners may advantageously be selected from the group formed by organic or inorganic thickeners and hydrocolloids. Suitable organic hydrocolloids include neutral, anionic and also cationic and amphoteric hydrocolloids, wherein both linear as well as cross-polymers have proved to be suitable hydrocolloids and thickeners for the emulsions of the invention. Suitable inorganic thickeners include purely inorganic thickeners as well as organically modified thickeners and hydrocolloids.

Furthermore, synergistic combinations within both groups as well as from both groups may advantageously be employed.

Examples in this case that can be cited are associative thickeners such as acryl-, methacryl-, maleic-acid homo- and/or copolymerisates, polyurethane derivatives, acrylamide derivatives, non-associative thickeners such as swellable thickeners based on acryl-, methacryl-, maleic-acid homo- or copolymers and derivatives thereof, cellulose and cellulose derivatives (carboxymethyl cellulose, hydroxyethyl cellulose, methyl cellulose, methylhydroxyethyl cellulose, methylhydroxypropyl cellulose, ethylhydroxyethyl cellulose, hydrophobically modified ethylhydroxyethyl cellulose, microcrystalline cellulose, cellulose gum and mixtures of these two with different ratios of microcrystalline cellulose to cellulose gum, hydrophobically modified hydroxyethyl cellulose), clays (phyllosilicates, smectite, aluminosilicates or phyllosilicates such as montmorillonite, bentonite, hectorite, attapulgite) as well as magnesium aluminium silicate and organo-clay derivatives (organically modified aluminosilicates, bentonite, hectorite) and also silica derivatives (fumed silica), organowaxes (castor oil derivatives, polyamide-based organowaxes), polyesteramides and organometallic thickeners (titanates and zirconates)—particularly in combination with starch and cellulose derivatives, natural gum derivatives such as guar or starch derivatives.

Particularly suitable members of the gum group are natural and modified polymers, preferably of vegetable origin such as gum arabic, which can be produced from various types of acacia. Gums can also be obtained from other trees, for example gum tragacanth. Alginates and carrageenan and their derivatives are also suitable. Xanthan gum and its variations and derivatives are also particularly suitable as hydrocolloids and thickeners. Guar, carouba and pectin also fall into the gum group and are suitable.

Natural polymers which are suitable as thickeners and hydrocolloids also include starches and their derivatives (dextrin derivatives) such as carboxymethyl starches, hydroxymethyl starches and also phosphated starches.

Electrolytes, be they monovalent or multivalent, are tolerated up to a concentration of approximately 40%, preferably up to 20% and particularly preferably up to 15% without significantly influencing the self-emulsifying mechanism and the emulsions obtained.

Cosmetic and dermatological preparations may contain cosmetic excipients that are in normal use in such preparations, for example preservatives, bactericides, fragrances, foam inhibitors; dyes, pigments which produce a colouring effect, thickening agents, softening, moisturizing and/or moisture-retaining substances, organic solvents, active substances, such as vitamins and their derivatives, plant extracts, enzymes, steroids and their derivatives and/or ceramides and their derivatives.

Particularly preferred applications are as follows:

emulsions for personal care and cosmetics;

foodstuff applications;

auxiliary substances for textiles and leather;

emulsions for the agricultural field;

emulsions for metalworking;

silicone oil emulsions in water;

emulsions for construction chemistry;

emulsions for household and vehicle care (furniture care, car interiors and exteriors);

emulsions for shoe and textile care;

emulsions for the manufacture of technical textiles;

emulsions of fluorinated hydrocarbons and derivatives;

emulsions of polymers for sealing, varnishing and adhesive applications;

emulsions of polymers for nonwovens, wall and other surface coverings.

The following examples illustrate the invention (%=weight %):

EXAMPLE 1

Emulsion Base for Personal Care Applications, for Example

| | | |
|---|---|---|
| A) | Imwitor 560 (Na-Lauroyl Lactylate) | 1.9% |
| | Emuldac AS 80 (C 16-18-alcohol polyethylene Glycolether (>50 EO)) | 0.9% |
| | Glycerin | 1.8% |
| | Water (Aqua), deionized | 2.7% |
| B) | MIGLYOL ® 812 (Caprylic/Capric Triglyceride) | 41.6% |
| C) | Water (Aqua), deionized | 51.1% |

Preparation:

Mix phase A homogeneously. Slowly add phase B, with stirring, in a laminar flow field (ca. 1500 rpm; wire stirrer), continue mixing for 1 min. Add phase C, with stirring. The emulsion has a mean droplet size (D50, determined by statistical laser light scattering in accordance with DIN/ISO 13320) of 400 nm.

EXAMPLE 2

Personal Care Basic Milk

| | | |
|---|---|---|
| A) | Imwitor 560 (Na-Lauroyl Lactylate) | 0.5% |
| | MARLIPAL O13/120 (Trideceth-12) | 0.25% |
| | Glycerin | 0.33% |
| | Water (Aqua), deionized | 0.92% |
| B) | MIGLYOL ® 8810 (Butylene Glycol Dicaprylate/Dicaprate) | 1.5% |
| | COSMACOL ® EMI (C12-13 Alkyl Malate) | 1.0% |
| | DYNACERIN ® 660 (Oleyl Erucate) | 1.0% |
| | Mineral oil (Paraffinium Liquidium) | 6.5% |
| C) | Water (Aqua), deionized | 73.8% |
| | Keltrol (Xanthan Gum) | 0.3% |
| | Glycerin | 2.0% |
| D) | Carbopol Ultrez 21 polymer (3%) (Carbomer) | 10.0% |
| E) | NaOH (10%) | 1.2% |
| F) | Phenonip (Phenoxyethanol, Methylparaben, Ethylparaben, Butylparaben, Propylparaben and Isobutylparaben | 0.7% |

Preparation: Mix phase A homogeneously. Mix phase B homogeneously. Slowly add phase B to phase A with stirring in a laminar flow field (ca. 1500 rpm; wire stirrer), continue mixing for 1 min. Mix phase C, add with stirring. Add phase D with stirring, add phase E with stirring, add phase F with stirring. The emulsion has a mean droplet size of 340 nm.

EXAMPLE 3

Emulsion for Personal Care Wet Wipes

| | | |
|---|---|---|
| A) | MWITOR 380 (Glyceryl Cocoate/Citrate/Lactate) | 2.0% |
| | Glucopon 215 CS UP (Capryl Glucoside) | 1.0% |
| | Decaglyn 1-L (Polyglycery-10 Laurate) | 0.3% |
| | Glycerin | 1.3% |
| | Water (Aqua), deionized | 3.2% |
| B) | MIGLYOL(R) 812 (Caprylic/Capric Triglyceride) | 29.7% |
| C) | Water (Aqua), deionized | 62.5% |

Preparation: Mix phase A homogeneously. Slowly add phase B to phase A with stirring in a laminar flow field (ca. 1500 rpm; wire stirrer), continue mixing for 1 min. Add phase C with stirring. The emulsion has a mean droplet size of 400 nm.

EXAMPLE 4

Cosmetic O/W Lotion

| | | |
|---|---|---|
| A) | AMPHOLYT JB 130 K (cocoamidopropyl betaine) | 2.7% |
| | Glycerin | 3.8% |
| B) | MIGLYOL(R) 812 (Caprylic/Capric Triglyceride) | 4.0% |
| | Dicapryl Ether | 6.3% |
| | Cetearyl Isononanoate | 3.0% |
| | Isopropyl Palmitate | 8.0% |
| | Cyclomethicone | 2.0% |
| C) | Water (Aqua), deionized | 20.0% |
| | Carbomer | 0.3% |
| D) | Water (Aqua), deionized | 48.8% |
| | TEA | 0.2% |
| | Panthenol | 0.3% |
| | Phenonip | 0.7% |

Preparation: Firstly, phase C is produced. To this end, the carbomer is completely swollen with stirring. Phases A and B are each homogeneously mixed and heated to 70° C. Phase B is slowly added to phase A, with stirring in a laminar flow field. After addition, depending on the size of the batch, homogenization is carried out briefly by stirring (laminar flow conditions must be maintained). Next, phases C and D are stirred in one after the other. The emulsion has a mean droplet size of 700 nm.

EXAMPLE 5

Cosmetic O/W Lotion (Also Sodium Alkyl Phosphates)

| A) | Servoxyl VPDZ 6/100 (Sodium Isotrideceth-6 Phosphate) | 0.30% |
|---|---|---|
| | Triethanolamine | 0.08% |
| | Coconut fat + 150 EO | 0.63% |
| | Glycerin | 2.98% |
| | Demin. water | 1.06% |
| B) | MIGLYOL(R) 812 (Caprylic/Capric Triglyceride) | 7.07% |
| | Octyl Stearate | 8.49% |
| | Shea Butter | 4.71% |
| | COSMACOL ECI (Tri-C12-C13 Alkyl Citrate) | 3.77% |
| | COSMACOL EMI (Di-C12-C13 Alkyl Malate) | .77% |
| | Fragrance, mandarin & neroli (Symrise) | 0.47% |
| C) | Water (Aqua), deionized | 66.70% |
| | Carbomer (Acrylates/C10-30 Alkyl Acrylate Crosspolymer) | 0.40% |
| | NaOH | 0.20% |
| | Phenonip | 1.00% |

Preparation: Firstly, phase C is produced. To this end, the carbomer is completely swollen with stirring. Phases A and B are each homogeneously mixed and heated to 70° C. Phase B is slowly added to phase A, with stirring in a laminar flow field. After addition, depending on the size of the batch, homogenization is carried out briefly by stirring (laminar flow conditions must be maintained). Next, phase C is stirred in. The emulsion has a mean droplet size of 286 nm.

EXAMPLE 6

Emulsion for Foodstuffs (Food Contact) Applications

| A) | ANIODAC AGCK-38 (Coco potassium soap, aqueous solution) | 3.4% |
|---|---|---|
| | IMWITOR 380 (Glyceryl Cocoate/Citrate/Lactate) | 0.6% |
| | Glycerin | 1.1% |
| B) | MIGLYOL ® 812 (Caprylic/Capric Triglyceride) | 4.1% |
| C) | Water (Aqua), deionized | 0.8% |

Preparation: Mix phase A homogeneously. Slowly add phase B to phase A with stirring in a laminar flow field (ca. 1500 rpm; wire stirrer), continue mixing for 1 min. Add phase C with stirring. The emulsion has a mean droplet size of 400 nm.

EXAMPLE 7

Cooling Lubricant Emulsion

| A) | MARLOWET 4539 (isononanol, ethoxylated, propoxylated, carboxymethylated) | .6% |
|---|---|---|
| | MARLOSOL FS (oleic acid-polyethylene glycol diester) | 1.2% |
| | Glycerin | 1.2% |
| | Water (Aqua), deionized | 1.8% |
| B) | Shell Gravex 915 | 46.3% |
| C) | Water (Aqua), deionized | 48.9% |

Preparation: Mix phase A homogeneously. Slowly add phase B to phase A with stirring in a laminar flow field (ca. 1500 rpm; wire stirrer), continue mixing for 1 min. Add phase C with stirring. The emulsion has a mean droplet size of 800 nm.

EXAMPLE 8

Forming Oil Emulsion for Construction Chemistry

| A) | Servoxyl VPDZ 100 (C13 alcohol polyethylene glycol ether (6 EO) phosphate ester) | 0.2% |
|---|---|---|
| | Triethanolamine | 0.1% |
| | PEG23 Lauryl Alcohol | 0.5% |
| | Water, deionized | 2.7% |
| B) | Forming oil | 20.0% |
| C) | Water, deionized | 76.5% |

Preparation: Mix phase A homogeneously. Slowly add phase B to phase A with stirring in a laminar flow field (ca. 1500 rpm; wire stirrer), continue mixing for 1 min. Add phase C with stirring. Mean droplet size of emulsion 280 nm.

EXAMPLE 9

Silicone Oil Emulsion

| A) | MARLINAT 242/90M (MIP A-Laureth Sulphate (and) Propylene Glycol) | 1.5% |
|---|---|---|
| | COSMACOL ELI (C12-13 Alkyl Lactate) | .7% |
| | Glycerin | 3.1% |
| | Water (Aqua), deionized | 0.1% |
| B) | acker silicone oil AK 300.000 | 51.0% |
| C) | Water (Aqua), deionized | 43.4% |
| | Keltrol (Xanthan Gum) | 0.2% |

Preparation: Mix phase A homogeneously. Slowly add phase B to phase A with stirring in a laminar flow field (ca. 1500 rpm; wire stirrer), continue mixing for 1 min. Add phase C with stirring. The emulsion has a mean droplet size of 900 nm.

EXAMPLE 10

Silicone Oil Emulsion

| A) | MARLINAT 242/90M (MIPA-Laureth Sulphate (and) Propylene Glycol) | 1.5% |
|---|---|---|
| | MARLOWET COE 145 (coconut oil polyalkylene glycol ester) | 0.7% |
| | Glycerin | 2.6% |
| | Water (Aqua), deionized | 0.7% |
| B) | Wacker silicone oil AK 300.000 | 61.1% |
| C) | Water (Aqua), deionized | 33.3% |

Preparation: Mix phase A homogeneously. Slowly add phase B to phase A with stirring in a laminar flow field (ca. 1500 rpm; wire stirrer), continue mixing for 1 min Add phase C with stirring. The emulsion has a mean droplet size of 1400 nm.

EXAMPLE 11

Silicone Oil Emulsion

| | | |
|---|---|---|
| A) | MARLINAT 242/90M (MIPA-Laureth Sulphate (and) Propylene Glycol) | 2.1% |
| | SAFOL 23 ($C_{12/13}$ alcohol) | 0.9% |
| | Glycerin | 3.4% |
| | Water (Aqua), deionized | 1.0% |
| B) | Abil 350 (polydimethylsiloxane) | 40.3% |
| C) | Water (Aqua), deionized | 52.3% |

Preparation: Mix phase A homogeneously. Slowly add phase B to phase A with stirring in a laminar flow field (ca. 1500 rpm; wire stirrer), continue mixing for 1 min. Add phase C with stirring. The emulsion has a mean droplet size of 200 nm.

The invention claimed is:

1. A method for producing oil-in-water dispersions from self-emulsifying gel concentrates, comprising performing the following steps in the order recited:
    (a) providing an emulsifier concentrate (A) comprising at least:
    (A.1) 0.1 to 75% by weight of one more polyols (P);
    (A.2) 5 to 80% by weight of water (W); and
    (A.3) 5 to 40% by weight of a surfactant selected from ionic surfactants (I), non-ionic surfactants (N), and mixtures thereof;
    each with respect to the emulsifier concentrate (A);
    (b) bringing an oil phase (O) into contact with the emulsifier concentrate (A) in a laminar flow field in order to obtain a self-emulsifying O/W gel concentrate (G) with an oil content of more than 5% by weight; and
    (c) bringing the O/W gel concentrate (G) into contact with water to produce an oil-in-water dispersion without the input of mechanical energy, wherein the oil-in-water dispersion is an emulsion and the oil phase (O) is the disperse phase,
    wherein the surfactant comprises at least an anionic surfactant (AS).

2. The method according to claim 1, characterized in that the O/W gel concentrate (G) has an oil content of 60to 99% by weight.

3. The method according to claim 1, characterized in that the O/W gel concentrate self-actingly incorporates into water without the action of shear forces to obtain a macro-emulsion (M), in the thermodynamic sense.

4. The method according to claim 1, characterized in that the water in step (c) contains less than 5% by weight of additives.

5. The method according to claim 1, characterized in that the oil phase comprises at least one of:

triglycerin esters of C8- to C24- carbonic acids;
di-, tri- or poly-hydroxy compounds at least partially esterified with C6 to C32 carbonic acids or C6 to C32 hydroxycarbonic acids;
C12-C15- alkylbenzoates;
di-(C12-C32)ethers;
esters having 32 and more carbon atoms;
silicone oils, in particular polydimethylsiloxane; and
mixtures thereof.

6. The method according to claim 1, characterized in that the O/W gel concentrate contains thickener[s].

7. The method according to claim 1, characterized in that said ionic surfactant is used together with a branched fatty alcohol containing at least 8 carbon atoms.

8. The method according to claim 1, characterized in that the oil-in-water dispersion has at least 50% to 98% by weight of water and 1% to 50% by weight of oil.

9. The method according to claim 1, characterized in that the polyol is glycerin.

10. The method according to claim 3, characterized in that the O/W gel concentrate self-actingly incorporates into water without the action of shear forces to obtain a nano emulsion (C).

11. The method according to claim 5, characterized in that the triglycerin esters are of C12 to C18 carbonic acids.

12. The method according to claim 1, wherein the emulsifier concentrate (A) comprises:
    (A.2) 50 to 70% by weight of water (W); and
    (A.3) 10 to 30% by weight of a surfactant selected from ionic surfactants (I), non-ionic surfactants (N), and mixtures thereof.

13. The method of claim 1, wherein the oil-in-water dispersion is a nano-emulsion comprising oil droplets having a size below 1000 nm.

14. A method for producing oil-in-water dispersions from self-emulsifying gel concentrates, comprising performing the following steps in the order recited:
    (a) providing an emulsifier concentrate (A) comprising at least:
    (A.1) 0.1 to 75% by weight of one more polyols (P);
    (A.2) 5 to 80% by weight of water (W); and
    (A.3) 5 to 40% by weight of a surfactant;
    each with respect to the emulsifier concentrate (A);
    (b) bringing an oil phase (O) into contact with the emulsifier concentrate (A) in a laminar flow field in order to obtain a self-emulsifying O/W gel concentrate (G) with an oil content of more than 5% by weight; and
    (c) bringing the O/W gel concentrate (G) into contact with water to produce an oil-in-water dispersion without the input of mechanical energy, wherein the oil-in-water dispersion is an emulsion and the oil phase (O) is the disperse phase,
    wherein the surfactant is selected from an anionic surfactant (AS), a mixture of anionic surfactants, a non-ionic surfactant (N), a mixture of non-ionic surfactant, and mixtures thereof.

* * * * *